(12) United States Patent
Manne et al.

(10) Patent No.: US 7,074,818 B2
(45) Date of Patent: Jul. 11, 2006

(54) CRYSTALLINE FORMS VI AND VII OF ATORVASTATIN CALCIUM

(75) Inventors: Satyanarayana Reddy Manne, Hyderabad (IN); Nagaraju Chakilam, Secunderabad (IN); Srinivasulu Gudipati, Hyderabad (IN); Srinivas Katkam, Secunderabad (IN); Rajeswar Reddy Sagyam, Mahaboob Nagar (IN)

(73) Assignees: Dr. Reddy's Laboratories Limited, Hyderabad (IN); Dr. Reddy's Laboratories, Inc., Upper Saddle River, NJ (US)

( * ) Notice: Subject to any disclaimer, the term of this patent is extended or adjusted under 35 U.S.C. 154(b) by 0 days.

(21) Appl. No.: 10/483,580

(22) PCT Filed: Jan. 7, 2002

(86) PCT No.: PCT/US02/00431

§ 371 (c)(1),
(2), (4) Date: Jul. 1, 2004

(87) PCT Pub. No.: WO03/011826

PCT Pub. Date: Feb. 13, 2003

(65) Prior Publication Data

US 2004/0242899 A1    Dec. 2, 2004

(30) Foreign Application Priority Data

Jul. 30, 2001  (IN) .............................. 620/MAS/01

(51) Int. Cl.
*A61K 31/40* (2006.01)
*C07D 207/00* (2006.01)

(52) U.S. Cl. ...................................... 514/422; 548/537

(58) Field of Classification Search ................ 514/422; 548/537

See application file for complete search history.

(56) References Cited

U.S. PATENT DOCUMENTS

| 5,273,995 | A | * | 12/1993 | Roth ........................... 514/422 |
| 5,298,627 | A | * | 3/1994 | Butler et al. ................. 548/517 |
| 6,528,661 | B1 | * | 3/2003 | Niddam et al. .............. 548/537 |
| 6,600,051 | B1 | * | 7/2003 | Tully ........................... 548/537 |
| 6,605,728 | B1 | * | 8/2003 | O'Connell et al. .......... 548/537 |
| 6,605,729 | B1 | * | 8/2003 | Byrn et al. ................... 548/537 |
| 6,730,797 | B1 | * | 5/2004 | O'Connell et al. .......... 548/537 |
| 6,777,552 | B1 | * | 8/2004 | Niddam-Hildesheim et al. 544/332 |

FOREIGN PATENT DOCUMENTS

| WO | 97/03958 A | 2/1997 |
| WO | 97/03959 A | 2/1997 |
| WO | 01/36384 A | 5/2001 |
| WO | 02/41834 A | 5/2002 |
| WO | 02/43227 A | 6/2002 |
| WO | 02/43732 A | 6/2002 |
| WO | 02/051804 A | 7/2002 |
| WO | 02/057229 A | 7/2002 |

* cited by examiner

*Primary Examiner*—Kamal A. Saeed
*Assistant Examiner*—Susannah L. Chung
(74) *Attorney, Agent, or Firm*—Robert A. Franks; Edward D. Pergament; Milagros A. Cepeda

(57) ABSTRACT

The present invention relates to novel crystalline forms of atorvastatin calcium and to the methods of their production and isolation. More specifically, the present invention relates to novel Forms VI and VII of R—(R*,R*)]-2(4-fluorophenyl)-B,d dihydroxy-5(1-methylethyl)-3-phenyl-4-[(phenylamino)carbonyl]-1-H-pyrrole-1-heptanoic- acid calcium salt and hydrates thereof and to methods of their preparation.

8 Claims, 2 Drawing Sheets

CRYSTALLINE FORMS VI AND VII OF ATORVASTATIN CALCIUM

FIELD OF THE INVENTION

Figure 1:
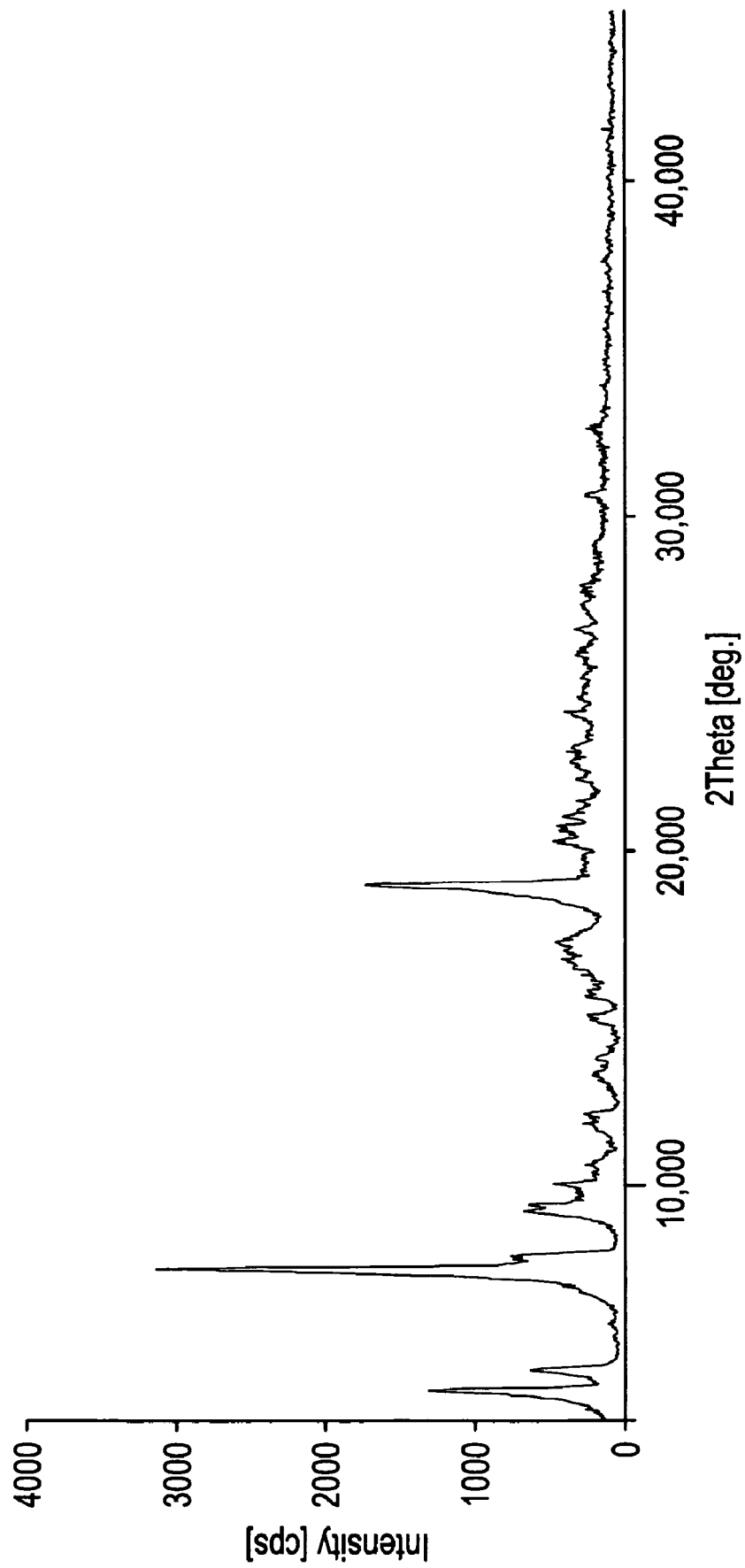

The present invention relates to novel crystalline forms of Atorvastatin calcium and to the methods of their production and isolation.

More specifically, the present invention relates to novel Forms VI and VII of R—(R*,R*)]-2(4-fluorophenyl)-β,δ-dihydroxy-5-(1-methylethyl)-3-phenyl-4-[(phenylamino)carbonyl]-1-H-pyrrole-1-heptanoic acid calcium salt and hydrates thereof and to methods of their preparation.

BACKGROUND OF THE INVENTION

Chemically Atorvastatin is R—(R*,R*)]-2-(4-fluorophenyl)-β, δ-dihydroxy-5-(1-methylethyl)-3-phenyl-4[(phenylamino)carbonyl]-1H-pyrrole-1-heptanoic acid. Atorvastatin is marketed as the hemi calcium salt trihydrate under the name LIPITOR by Warner Lambert Co and may be represented by Formula 1.

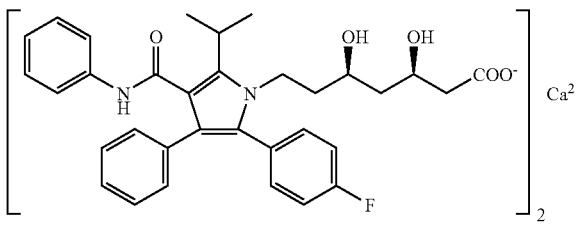

Atorvastatin is a member of the class of drugs called statins. Statin drugs are currently the most therapeutically effective drugs available for reducing low density lipoprotein (LDL) particle concentration in the blood stream of patients at risk for cardiovascular disease. A high level of LDL in to bloodstream has been linked to the formation of coronary lesions, which obstruct the flow of blood and can rupture and promote thrombosis; Goodman Gilman, *The Pharmacological Basis of Therapeutics* 879 (9th ed. 1996). Reducing plasma LDL levels has been shown to reduce the risk of clinical events in patients with cardiovascular disease and patients who are free of cardiovascular disease but who have hypercholesterolemia; Scandinavian Simvastatin Survival Study Group, 1994; Lipid Research Clinics Program, 1984a, 1984b.

U.S. Pat. No. 5,969,156 to Warner-Lambert Company, discloses crystalline Form I Atorvastatin hydrate, crystalline Form II Atorvastatin and hydrates thereof and crystalline Form IV Atorvastatin and hydrates thereof, which are useful as inhibitors of enzyme 3-hydroxy-3methylglutaryl-coenzyme A reductase (HMG-CoA reductase) and are hence useful hypolipidemic and hypocholesterolemic agents.

U.S. Pat. No. 6,121,461 also to Warner-Lambert Company, discloses crystalline Form III Atorvastatin hydrate, which is also a useful hypolipidemic and hypocholesterolemic agent.

WO 01/36384 A1 to Teva Pharmaceutical Industries Ltd discloses Form V Atorvastatin calcium and hydrates thereof; its preparation and a pharmaceutical composition thereof.

A process for the preparation of hydrated and anhydrous amorphous Atorvastatin is disclosed in U.S. Pat. No. 6,087,511 also to Warner-Lambert Company.

WO 01/28999 A1 to Egis Gyogyszergyarrt discloses a process for the preparation of amorphous Atorvastatin calcium.

It is also noteworthy to point out that U.S. Pat. No. 5,969,156 designates the Atorvastatin formed by prior art process (viz U.S. Pat. Nos. 5,003,080; 5,097,045; 5,103,024; 5,124,482; 5,149,837; 5,155,251; 5,216,174; 5,245,047; 5,248,793; 5,280,126; 5,397,792; and 5,342,952) as amorphous Atorvastatin which has unsuitable filtration and drying characteristics for large scale production and which must be protected from light, heat, oxygen and moisture (column 1; lines 62–65).

Atorvastatin is prepared as its calcium salt, which is desirable since it enables Atorvastatin to be conveniently formulated for oral administration. There is hence a need to produce Atorvastatin calcium in a pure and crystalline form to enable formulations to meet exacting pharmaceutical requirements and specifications.

Furthermore, the process by which the crystalline form of Atorvastatin calcium is produced needs to be one, which is amenable to large-scale production. Additionally, it is desirable that the product should be in a form that is readily filterable and easily dried. Finally, it is economically desirable that the product be stable for extended periods of time without the need for specialized storage conditions.

The main aspect of the present invention is to provide novel crystalline forms of Atorvastatin calcium and hydrates thereof, and to a method for their preparation.

Another aspect of the present invention is that, the novel crystalline forms of Atorvastatin calcium and hydrates thereof are obtained in high purity. The generally preferred HPLC purity of crystalline Form VI and VII of Atorvastatin calcium and hydrates thereof, of the present invention is greater than 99.0% more preferably greater than 99.5%. Most pharmaceutical formulation processes are facilitated by use of the active materials that are free flowing high melting solids. The novel crystalline forms of Atorvastatin calcium of the present invention are high melting solids, very suited for formulation. The residual solvents associated with the novel forms, Form VI and Form VII are also very well within permissible limits and that again renders the novel crystalline forms suited for formulations.

SUMMARY OF THE INVENTION

Accordingly, the present invention is directed to novel crystalline forms of Atorvastatin calcium and hydrates thereof. These crystalline forms of Atorvastatin calcium are designated as Form VI and Form VII for convenience.

The present invention further provides a process for the preparation of novel crystalline Form VI and Form VII of Atorvastatin calcium and hydrates thereof, which is a commercially viable process well suited for industrial scale up.

BRIEF DESCRIPTION OF ACCOMPANYING DRAWINGS

FIG. 1 is a characteristic X ray powder diffractogram of novel crystalline Atorvastatin calcium Form VI. Vertical axis: Intensity (CPS); Horizontal axis: Two Theta (degrees). The significant d values (A°) obtained are 22.52, 19.44, 11.84, 11.23, 9.58, and 4.69.

Figure 2:
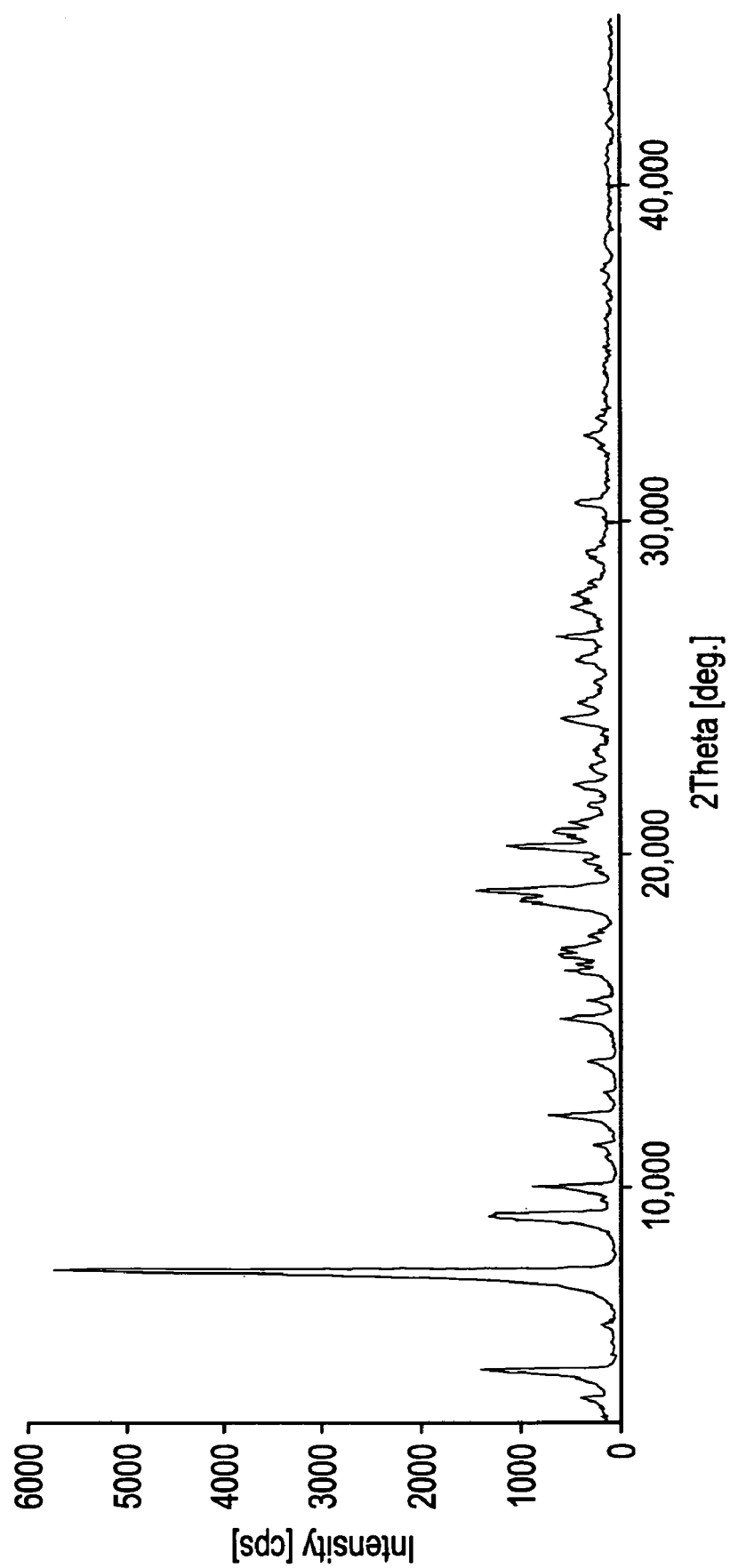

FIG. 2 is a characteristic is an X ray powder diffractogram of novel crystalline Atorvastatin calcium Form VII. Vertical axis: Intensity (CPS); Horizontal axis: Two Theta (degrees). The significant d values (A°) obtained are 19.36, 11.80 9.60, 4.75, 4.69 and 4.39.

DETAILED DESCRIPTION OF THE INVENTION

The present invention is directed to novel crystalline forms of Atorvastatin calcium and hydrates thereof. More particularly, the hydrates contain 1 to 4 moles of water. The crystalline Form VI and Form VII of the present invention may be characterized by their X Ray powder diffraction. Thus the X-Ray diffraction patterns of Form VI and VII of Atorvastatin calcium and their hydrates were measured on a Rigaku D/Max 2200 Powder Diffractometer with Cu Radiation source. Crystalline Form VI has X-ray powder diffraction pattern essentially as shown in the Table 1. The X-ray powder diffraction pattern is expressed in terms of the 2Θ, d-spacings, and relative intensities >15%.

| 2Θ | d-spacings | Intensity, $I/I_0$, % |
|---|---|---|
| 3.92 | 22.52 | 40 |
| 4.54 | 19.44 | 17 |
| 7.46 | 11.84 | 100 |
| 7.86 | 11.23 | 21 |
| 9.22 | 9.58 | 19 |
| 18.9 | 4.69 | 55 |

Table 2 lists the 2Θ, d-spacings, and relative intensities >15% for crystalline Form VII of Atorvastatin calcium.

| 2Θ | d-spacings | Intensity, $I/I_0$, % |
|---|---|---|
| 4.56 | 19.36 | 21 |
| 7.48 | 11.80 | 100 |
| 9.20 | 9.60 | 21 |
| 18.64 | 4.75 | 15 |
| 18.88 | 4.69 | 24 |
| 20.20 | 4.39 | 17 |

The present invention is also directed to processes for preparation of novel crystalline forms of Atorvastatin calcium and hydrates thereof.

The present invention hence, provides a process for the preparation of crystalline Form VI of Atorvastatin calcium, which comprises:

a. heating a mixture of [R—(R*,R*)]-2-(4-fluorophenyl)-β,δ-dihydroxy-5-1-methyl ethyl-3-phenyl-4-[(phenyl amino)-carbonyl]-1H-pyrrole-1-heptanoic acid, tertiary butyl ester (hereinafter referred to as "ester" or "active ingredient" for convenience), acetonitrile and sodium hydroxide flakes to about 25–60° C.;

b. maintaining the reaction mixture of step a) at 25–60° C. for about 3–9 hours preferably 6 hours;

c. adding to the above reaction mixture an aqueous solution of calcium acetate hemihydrate;

d. further stirring the reaction mixture at 30–50° C. for about 30 minutes to 2 hours, preferably 45 minutes;

e. filtering the reaction solution obtained in step d) through hyflow bed;

f. distilling the solvent from reaction solution of step e) to yield a residue;

g. suspending the residue of step f) in a mixture of aliphatic nitrile solvent selected from acetonitrile and propionitrile; and water, in a ratio of 1:0.1–2, such that the volume of the mixture of solvent-water is 18–40 times the weight of ester in step a); (The ratio of active ingredient to the mixture of solvent and water is 1:18–40 (wt/vol)).

h. refluxing the reaction mixture obtained in step g) for 10–18 hours preferably 12–14 hours; and i. isolating the crystalline Form VI of Atorvastatin calcium, obtained in step h) by filtration or other conventional methods known in the art.

In step a) of the process an ester with an alkyl group of 1–10 carbon atoms, allyl or benzyl group can be used in place of the tertiary butyl ester and another nitrile such as propionitrile can be used in place of acetonitrile. The ratio of solvent to active ingredient in step a) is 16 times the active ingredient (wt:volume) (gm:ml).

In step a) the molar ratio of active ingredient to base is 1:1–1.5 preferably 1:1.15.

In step a) other alkali hydroxides can be used in place of sodium hydroxide. The alkali hydroxides including the sodium hydroxide may be in any form and the form is not limited to flakes.

The following organic and inorganic salts of calcium may be used in place of calcium acetate hemihydrate:

Organic salts such as carboxylates and sulphonates. The carboxylates may be selected from acetate, propionate, butyrate, tartarate; aryl carboxylates like benzoate and phthlate as well as higher carboxylates like Stearate or dodecanoate. Also included are succinate and ascorborate.

Sulphonates may be selected from lower alkyl and aryl sulfonates like calcium methane sulfonates, calcium benzene sulfonates and calcium para toluenesulfonates.

Inorganic salts of calcium may be selected from calcium chloride, fluoride, bromide, iodide and calcium borate and tetra fluoro borate, calcium carbonate, mono, di and tri basic calcium phosphate, calcium sulfate and calcium hydroxide and hydrates thereof.

The molar ratio of active ingredient to calcium acetate hemihydrate or calcium salt is 1:0.5–0.7 preferably 1:0.6.

The present invention also provides a process for the preparation of crystalline Form VII of Atorvastatin calcium, which comprises:

a. suspending residue (prepared as per steps a–f for crystalline form VI) in a mixture of water and organic solvent such as an amide solvent such as dimethyl formamide or an aliphatic nitrile solvent selected from acetonitrile or propionitrile; in a ratio of organic solvent to water 1:0.1–5 (vol/vol) such that the volume of the mixture of solvent—water is 5 to less than 10 times, the weight of initial ester used in the preparation of crystalline form VI (vol:wt) (ml/gm);

b. refluxing the reaction mixture obtained in step a) for 10 minutes to 1 hour preferably 30 minutes;

c. subsequently, adding a second mixture of organic solvent: water (1:0.01–1) (vol/vol); such that the volume of the mixture of solvent—water is 5–10 times the weight of the initial ester; and refluxing the reaction mixture for 10 minutes to 1 hours, preferably 30 minutes;

d. finally, adding a third mixture of organic solvent: water (1:0.01–1) (vol/vol); such that the volume of mixture of solvent—water is 5–10 times the weight of the initial ester; and refluxing the reaction mixture for 1 hour to 3 hours, preferably 1 hour;

e. cooling the reaction mixture of step d) to 0–10° C. preferably below 5° C.; and f. isolating the crystalline Form VII of Atorvastatin calcium, obtained in step e) by filtration or other conventional methods known to art.

The organic solvents used in steps c) and d) for the preparation of crystalline Form VII of Atorvastatin calcium include amide solvents such as dimethyl formamide or aliphatic nitrile solvent selected from acetonitrile and propionitrile. The same solvent used in step a) is used in steps c) and d).

The present invention hence provides novel crystalline forms of Atorvastatin calcium and hydrates thereof, and to a method for their preparation, which is amenable to large-scale production.

The novel crystalline forms of Atorvastatin calcium of the present invention are readily filterable and easily dried.

Moreover, the HPLC purity of novel crystalline Form VI and VII of Atorvastatin calcium and hydrates thereof, of the present invention is greater than 99.0% more preferably greater than 99.5%.

The crystalline forms of Atorvastatin calcium of the present invention are also high melting solids with residual solvents within permissible limits and are very well suited for formulation. The crystalline Form VI of Atorvastatin calcium hydrate may contain 1 to 4 moles of water, preferably 3 moles of water. The crystalline Form VI of Atorvastatin calcium hydrate may contain 1 to 5 moles of water, preferably 3 moles of water.

EXAMPLES

The present invention is illustrated by the following examples, which are not intended to limit the effective scope of the invention.

Example 1

Preparation of Crystalline Form VI of Atorvastatin Calcium

A mixture of [R—(R*,R*)]-2-(4-fluoro phenyl)β,δ-dihydroxy-5-[(1-methyl ethyl)-3-phenyl-4[(phenyl amino)-carbonyl]-1H-pyrrole-1-heptanoic acid, tert. butyl ester (25.0 g), acetonitrile (400 ml) water (62 ml) and sodium hydroxide flakes (1.88 g) are heated to about 25–55° C. and maintained at the same temperature for about 4 and a half hours. To the reaction mixture is then added an aqueous solution of calcium acetate hemihydrate (4.0 g in 41.6 ml of water) and stirred at 30–50° C. for about 1 hour. Subsequently, the solution obtained is filtered through hyflow bed and washed with acetonitrile (125 ml). The solvent is then distilled completely to yield residue.

To the residue thus obtained, a mixture of acetonitrile: water (1:1) (500 ml) is added and the reaction mixture maintained at reflux for about 13 hours. The separated solid is then filtered at 70° C. and washed with a mixture of acetonitrile: water (1:1) (50 ml). The resultant solid is dried at 60–70° C. to render desired crystalline Form-VI of Atorvastatin Calcium.

HPLC Purity: 99.71%

Example 2

Preparation of Crystalline Form VII of Atorvastatin Calcium

A mixture of [R—(R*,R*)]-2-(4-fluoro phenyl)-β,δ-dihydroxy-5-[(1-methyl ethyl)-3-phenyl-4[(phenyl amino)-carbonyl]-1H-pyrrole-1-heptanoic acid, tert. butyl ester (25.0 g), acetonitrile (400 ml) and sodium hydroxide flakes (1.88 g) are heated to about 30–45° C. and maintained at the same temperature for about 6 hours. To the reaction mixture is then added an aqueous solution of calcium acetate hemihydrate (4.0 g in 41.6 ml of water) and stirred at 30–50° C. for about 50 minutes. Subsequently, the solution obtained is filtered through hyflow bed and washed with acetonitrile (125 ml). The solvent is then distilled completely to yield residue. To the residue thus obtained, a mixture of acetonitrile: water (1:1; 150 ml) was added and the reaction mixture maintained at reflux for about 15–20 minutes. Upon completion of this step, a second mixture of acetonitrile: water (1:1; 150 ml) is added to resultant slurry, and again the reaction mixture maintained at reflux about 30 minutes. Finally a third mixture of acetonitrile water (1:1; 150 ml) is added to resultant slurry, and the reaction mixture maintained at reflux for about 1 hour. The reaction mixture then cooled to 0–1° C., filtered and dried at 50–60° C. to get the desired crystalline Form VII of Atorvastatin Calcium.

HPLC Purity: 99.81%

Example 3

A mixture of [R—(R*,R*)]-2-(4-fluoro phenyl)-β,δ-dihydroxy-5-[(1-methyl ethyl)-3-phenyl-4[(phenyl amino)-carbonyl]-1H-pyrrole-1-heptanoic acid, tert. butyl ester (10.0 g), acetonitrile (80 ml) and sodium hydroxide flakes (0.75 g) in water (25.0 ml) are heated to about 35–45° C. and maintained at the same temperature for about 1–2 hours.

To the reaction mixture is then slowly added an aqueous solution of calcium acetate hemihydrate (1.6 g in 16.0 ml of water) at 35–45° C. for about 30–60 minutes. After another 15–20 minutes, the temperature is raised to 50–60° C. and the solution obtained is filtered through hyflow bed and washed with acetonitrile (10.0 ml). The solvent is then distilled completely to yield residue. To the residue thus obtained, is added acetonitrile (60 ml) and the temperature is raised to 50–60° C. and the solution obtained is again filtered through hyflow bed and washed with acetonitrile (10.0 ml). To the filtrate, water (120.0 ml) was added and the reaction mixture maintained at reflux about 60–90 minutes.

The reaction mixture is then cooled to 0–10° C., filtered and dried at 50–60° C. for 10–12 hours to get the desired crystalline Form VII of Atorvastatin Calcium.

Yield 7 to 9 gm HPLC Purity 99.7%

The invention claimed is:

1. A crystalline Form VI of Atorvastatin calcium hydrate, which is characterized by the following X-ray powder diffraction pattern (d values in A°): 22.52, 19.44, 11.84, 11.23, 9.58, and 4.69.

2. A process for preparing Form VI of Atorvastatin calcium of claim 1 or hydrates thereof, which comprises:
   a. heating a mixture of [R—(R*,R*)]-2-(4-fluorophenyl)-[β,δ-dihydroxy-5-[(1-methylethyl)-3-phenyl-4-[(phenylamino)-carbonyl]-1H-pyrrole-1-heptanoic acid, tert. butyl ester, acetonitrile and sodium hydroxide flakes to about 25–60° C.;
   b. maintaining the reaction mixture of step a) at 25–60° C. for about 3 to 9 hours;
   c. adding to the above reaction mixture an aqueous solution of calcium acetate hemihydrate;
   d. further stirring the reaction mixture at 30–50° C. for about 1–2 hours;
   e. filtering the reaction solution obtained in step d) through a hyflow bed;
   f. distilling the solvent from reaction solution of step e) to yield a residue;
   g. suspending the residue of step f) in a mixture of water and an aliphatic nitrile solvent selected from acetonitrile and propionitrile;
   h. refluxing the reaction mixture obtained in step g) for 10–18 hours; and i. isolating the crystalline Form VI of Atorvastatin calcium, obtained in step h).

3. The process as claimed in claim 2, wherein in step g) the ratio of nitrile solvent to water is 1:0.1–2.

4. The process as claimed in claim 2, wherein in step g) the volume of the mixture of solvent and water is 18–40 times the weight of the ester added in step a).

5. The process as claimed in claim 2, wherein in step a) the molar ratio of [R—(R*,R*)]-2-(4-fluorophenyl)-β,δ-dihydroxy-5-[(1-methylethyl)-3-phenyl-4-[(phenylamino)-carbonyl]-1H-pyrrole-1-heptanoic acid, tert butyl ester to sodium hydroxide is 1:1–1.5.

6. The crystalline Form VI of Atorvastatin calcium hydrate according to claim 1, which contains from 1 to 4 moles of water.

7. The crystalline Form VI of Atorvastatin calcium hydrate according to claim 1, which contains 3 moles of water.

8. A process for preparing Form VI of Atorvastatin calcium of claim 1 or hydrates thereof, which comprises:
   a. heating a mixture of [R—(R*,R*)]-2-(4-fluorophenyl)-β,δ-dihydroxy-5-[(1-methylethyl)-3-phenyl-4-[(phenylamino)-carbonyl]-1H-pyrrole-1-heptanoic acid, $C_1$–$C_{10}$ alkyl ester, allyl ester or benzyl ester; a nitrile and an alkali hydroxide to about 25–60° C.;
   b. maintaining the reaction mixture of step a) at 25–60° C. for about 3 to 9 hours;
   c. adding to the reaction mixture of step b) an aqueous solution of a calcium salt;
   d. further stirring the reaction mixture at 30–50° C. for about 1–2 hours;
   e. filtering the reaction solution obtained in step d) through a hyflow bed;
   f. distilling the solvent from reaction solution of step e) to yield a residue;
   g. suspending the residue of step f) in a mixture of an aliphatic nitrile solvent selected from acetonitrile or propionitrile and water;
   h. refluxing the mixture of step g) for 10–18 hours; and
   i. isolating the crystalline Form VI of Atorvastatin calcium.

* * * * *